United States Patent [19]

Romandi

[11] 4,317,039

[45] Feb. 23, 1982

[54] X-RAY DIAGNOSTIC GENERATOR

[75] Inventor: Denes Romandi, Erlangen, Fed. Rep. of Germany

[73] Assignee: Siemens Aktiengesellschaft, Berlin & Munich, Fed. Rep. of Germany

[21] Appl. No.: 207,739

[22] Filed: Nov. 17, 1980

Related U.S. Application Data

[63] Continuation of Ser. No. 40,640, May 21, 1979, abandoned.

[30] Foreign Application Priority Data

Jul. 14, 1978 [DE] Fed. Rep. of Germany ....... 2831093

[51] Int. Cl.³ .......................... A61B 6/00; H05G 1/12

[52] U.S. Cl. ..................................... 250/418; 250/421

[58] Field of Search ............... 250/401, 402, 408, 418, 250/421

[56] References Cited

U.S. PATENT DOCUMENTS 4,053,778 10/1977 Franke ................................ 250/402

4,117,334 9/1978 Strauts ................................ 250/402

*Primary Examiner*—Alfred E. Smith

*Assistant Examiner*—T. N. Grigsby

*Attorney, Agent, or Firm*—Hill, Van Santen, Steadman, Chiara & Simpson

[57] ABSTRACT

An inverter, with a frequency lying in the medium frequency range, and a mains rectifier are connected with the high-voltage transformer. Between the X-ray tube and the high voltage transformer there is disposed a high-voltage rectifier with a high-voltage filter member. There is likewise connected with the filament transformer an inverter with a frequency lying in the medium frequency range and a mains rectifier. Filter members are connected between the mains rectifiers and the inverters. Plural inverters with different phase may supply respective high voltage transformers, and each transformer may have a voltage doubler high voltage rectifier contributing to X-ray tube anode voltage.

2 Claims, 1 Drawing Figure

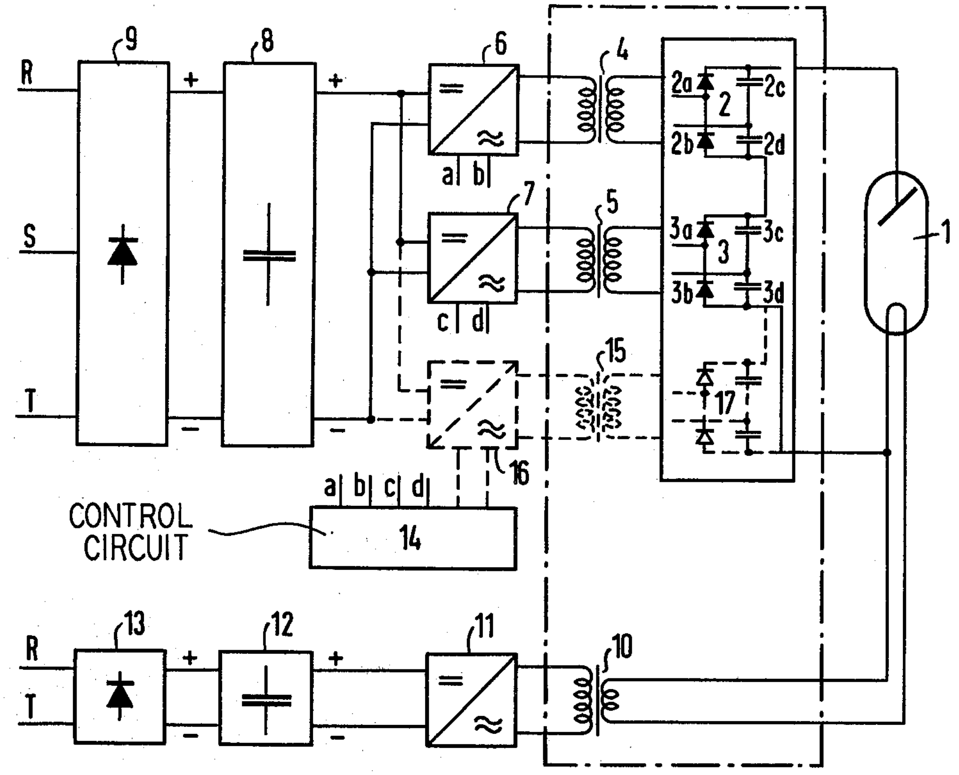
9
8
6
7
4
5
15
16
R
S
T
+
−
=
≈
a
b
c
d
2a
2b
2c
2d
2
3a
3b
3c
3d
3
17
1
CONTROL CIRCUIT
14
13
12
11
10

X-RAY DIAGNOSTIC GENERATOR

This is a continuation, of application Ser. No. 40,640, filed May 21, 1979 now abandoned.

BACKGROUND OF THE INVENTION

X-ray examination apparatus are known in which the patient is irradiated from different projections by a measuring arrangement consisting of an X-ray source and an X-ray detector and wherein the X-radiation received by the detector is converted into electric signals corresponding to the radiation intensity. In the case of these so-called computer tomographs, these electric signals are conveyed to a computer which calculates therefrom the attenuation coefficients of predetermined points of the examined transverse layer of the patient. These attenuation coefficients can be reproduced on a display apparatus in the form of an image of the examined transverse layer.

In the case of a computer tomography, it is necessary that the dose rate of the x-radiation emitted by the X-ray source be constant to a great degree, since fluctuations of the dose rate would bring about fluctuations of the output signals of the detector without density fluctuations in the patient being present. Thus, such fluctuations would falsify in the measurement result and would produce artifacts in the X-ray image.

SUMMARY OF THE INVENTION

The object underlying the invention consists in producing an X-ray diagnostic generator which manifests a high dose rate constancy and is therefore particularly suited for computer tomography. The X-ray diagnostic generator is intended to be substantially more favorable in terms of cost than the known generators having a high dose rate constancy.

An X-ray diagnostic generator which achieves this object is characterized in accordance with the invention by the combination of the following features:

It manifests a high voltage transformer to the input side of which there is connected an inverter, with a frequency lying in the medium frequency range, and a mains rectifier.

Between the X-ray tube and the high voltage transformer a high voltage rectifier with a high voltage filtering member is connected.

An inverter, with a frequency lying in the medium frequency range, and a mains rectifier are connected with the filament transformer for the X-ray tube.

Filtering members are connected between the mains rectifiers and the inverters.

Due to the arrangement of filter members in the low voltage and high voltage circuits, and the selection of a feed frequency which lies in the kHz-range in the high voltage circuit as well as in the filament circuit of the X-ray tube, the invention X-ray diagnostic generator manifests an extremely low ripple of the high voltage at the X-ray tube and hence a very high dose rate constancy, and is particularly suited for feeding the X-ray tube in the case of computer tomography.

A further reduction of the ripple of the high voltage at the X-ray tube and hence a further increase in the dose rate constancy is possible by virtue of the fact that several high voltage transformers are present each having a high-voltage rectifier connected at the output side; an inverter is connected at the input side of each high voltage transformer; and the outputs of the high-voltage rectifiers are connected with each other to increase the anode voltage; the output voltages of the inverters are chronologically offset relative to one another. In this embodiment of the invention, the frequency of the ripple of the high-voltage at the X-ray tube is substantially greater as compared with the utilization of a single high-voltage transformer with an input-connected inverter and an output-connected high-voltage rectifier. This high frequency is filtered out with a low outlay by means of the output-connected filter members and the capacitance of the high-voltage cable. As in the case of utilization of a single high-voltage transformer with a single input-connected inverter, the ripple of the mains voltage is filtered out by the filter member which is connected to the output of the mains rectifier.

In an embodiment of the invention, the high-voltage rectifier or rectifiers are voltage doubler circuits. In the case of this embodiment, the high-voltage transformer or transformers can be dimensioned for a high voltage which is lower than the high voltage at the X-ray tube and also lower than the output voltage of the high-voltage rectifier, or of one of the high-voltage rectifiers, respectively.

The invention shall be further explained in the following on the basis of an exemplary embodiment illustrated in the accompanying sheet of drawings; and other objects, features and advantages will be apparent from this detailed disclosure and from the appended claims.

BRIEF DESCRIPTION OF THE DRAWINGS

The single FIGURE is an electric circuit diagram showing a preferred embodiment in accordance with the present invention.

DETAILED DESCRIPTION

In the drawing, an X-ray tube 1 is illustrated which is fed by the series-connection of two high-voltage rectifiers 2 and 3. The high-voltage rectifiers 2 and 3 are voltage doublers and comprise rectifier elements *2a, 2b, 3a, 3b* and capacitor filter elements *2c, 2d, 3c, 3d.* They are connected to the secondary windings of two high-voltage transformers 4 and 5 whose primary windings are fed by inverters 6 and 7. The inverters 6 and 7 are parallel-connected at the output of a filter member 8 which is connected to a mains rectifier 9 for three-phase current.

The filament voltage for the X-ray tube 1 is supplied by filament transformer 10 which is fed by an inverter 11. The inverter 11 is supplied via a filter member 12 from a single phase-mains rectifier 13.

The inverters 6, 7, are controlled by a control circuit 14 in such a manner that their output voltages are chronologically offset relative to one another. The phase displacement amounts expediently to 90°, so that the ripple of the high-voltage at the X-ray tube 1, as compared with the instance in which only a single inverter and a single high-voltage transformer are provided, is reduced by the factor of two. The frequency of the ripple corresponds to double the inverter frequency.

It is possible within the framework of the invention, given a suitable dimensioning of the filter members in the high voltage circuit—which are components of the high voltage rectifiers 2, 3, in the exemplary embodiment—to provide only one inverter with one high voltage transformer. In addition, it is possible, in order to further reduce the ripple, and in order to increase the frequency of the ripple, to provide more than two high-voltage transformers with more than two inverters, as is indicated by the broken lines in the drawing for a third high-voltage transformer 15 and a third inverter 16.

In the exemplary embodiment, in that particular case wherein, in addition to the high-voltage transformers 4 and 5, yet further high-voltage transformers—e.g. the high-voltage transformer 15—are provided, a corresponding number of additional high-voltage rectifiers e.g. the high-voltage rectifier 17 is also present. The high-voltage rectifier 17 is to be connected into the circuit corresponding to the broken lines (illustrated), whereby the connection between the cathode of the X-ray tube 1 and the high-voltage rectifier 3 is eliminated.

The feed frequency of the high-voltage transformers 4, 5, 15, i.e., the frequency of the inverters 6, 7, 16, lies, as mentioned, in the medium frequency range and amounts to approximately six to seven kHz. The inverter 11 can also have the same frequency.

It will be apparent that many modifications and variations may be effected without departing from the scope of the novel concepts and teachings of the present invention.

I claim as my invention:

1. An X-ray diagnostic generator characterized by the combination of:

high-voltage transformer means (4, 5, 15), with first inverter means (6, 7, 16) operating at a frequency lying in the medium frequency range, and first power supply rectifier means (9) connected with the input side of the high-voltage transformer means:

an X-ray tube (1) with high-voltage rectifier means (2, 3, 17) connected between the high voltage transformer means and the X-ray tube;

a filament transformer (10) for the X-ray tube, with second inverter means (11) operating at a frequency lying in the medium frequency range, and a second power supply rectifier means (13) connected with the input side of the filament transformer; and filter circuit means (8, 12) connected between the power supply rectifier means (9, 13) and the inverter means (6, 7, 11, 16), said high-voltage transformer means comprising at least three high voltage transformers having at least three respective, individual primary windings, and said first inverter means comprising at least three separate inverters each connected to a respective one of said individual primary windings, and said individual inverters being operated out of phase with each other so as to supply output voltages to said individual primary windings having at least three respective different phase angles which are offset in phase relative to one another.

2. An X-ray diagnostic generator according to claim 1, with said high-voltage transformer means (4, 5, 15) having at least three individual secondary windings coupled with the respective individual primary windings, and said high-voltage rectifier means (2, 13, 17) comprising at least three voltage doubler circuits coupled with the respective individual secondary windings and connected in series across said X-ray tube (1).

* * * * *